United States Patent
Wu et al.

(10) Patent No.: US 11,766,189 B2
(45) Date of Patent: Sep. 26, 2023

(54) NUCLEAR MAGNETIC RESONANCE SYSTEM-BASED SUBSTANCE MEASUREMENT METHOD AND SYSTEM

(71) Applicant: WUXI MARVEL STONE HEALTHCARE CO., LTD., Wuxi (CN)

(72) Inventors: Ziyue Wu, Wuxi (CN); Hai Luo, Chengdu (CN); Weiqian Wang, Chengdu (CN); Xiao Chen, Chengdu (CN); Yang Ye, Wuxi (CN)

(73) Assignee: WUXI MARVEL STONE HEALTHCARE CO., LTD., Wuxi (CN)

( * ) Notice: Subject to any disclaimer, the term of this patent is extended or adjusted under 35 U.S.C. 154(b) by 0 days.

(21) Appl. No.: 18/068,133

(22) Filed: Dec. 19, 2022

(65) Prior Publication Data
US 2023/0157567 A1     May 25, 2023

Related U.S. Application Data

(63) Continuation of application No. PCT/CN2020/130163, filed on Nov. 19, 2020.

(30) Foreign Application Priority Data

Jun. 29, 2020 (CN) .......................... 202010611176.6

(51) Int. Cl.
| | |
|---|---|
| G01R 33/44 | (2006.01) |
| G01R 33/46 | (2006.01) |
| G01R 33/50 | (2006.01) |
| G01R 33/56 | (2006.01) |
| G01R 33/561 | (2006.01) |
| G01R 33/563 | (2006.01) |

(Continued)

(52) U.S. Cl.
CPC ............ *A61B 5/055* (2013.01); *G01R 33/448* (2013.01); *G01R 33/4625* (2013.01);
(Continued)

(58) Field of Classification Search
CPC .. A61B 5/055; G01R 33/448; G01R 33/4625; G01R 33/50; G01R 33/5608;
(Continued)

(56) References Cited

U.S. PATENT DOCUMENTS 7,622,919 B2    11/2009   Song et al.

FOREIGN PATENT DOCUMENTS

| CN | 1260581 C | 6/2006 |
|---|---|---|
| CN | 102116856 A | 7/2011 |

(Continued)

OTHER PUBLICATIONS

English translation of CN111351813A provided by Espacenet. (Year: 2023).*

(Continued)

*Primary Examiner* — Rishi R Patel (57) ABSTRACT

A nuclear magnetic resonance (NMR) system-based substance measurement method, including: acquiring several echo signals of an NMR pulse sequence varying in echo spacing from a substance to be measured followed by processing to obtain several signals varying in transverse relaxation and diffusion attenuation; and fitting, in combination with the prior knowledge, the signals to obtain the diffusion coefficient, transverse relaxation time or/and content weight of individual components of the substance to be measured. This application further provides a substance measurement system including a console, a magnet module, and an NMR system.

7 Claims, 5 Drawing Sheets

(51) Int. Cl.
  *G01N 24/08* (2006.01)
  *G01R 33/38* (2006.01)
  *A61B 5/055* (2006.01)
(52) U.S. Cl.
  CPC ............. *G01R 33/50* (2013.01); *G01N 24/08* (2013.01); *G01R 33/3808* (2013.01); *G01R 33/5608* (2013.01); *G01R 33/5617* (2013.01); *G01R 33/56341* (2013.01)
(58) Field of Classification Search
  CPC .......... G01R 33/5617; G01R 33/56341; G01R 33/3808; G01N 24/08
  See application file for complete search history.

(56) References Cited

FOREIGN PATENT DOCUMENTS

| CN | 105334239 A | | 2/2016 | |
| --- | --- | --- | --- | --- |
| CN | 106772645 A | | 5/2017 | |
| CN | 106814337 A | | 6/2017 | |
| CN | 108291440 A | | 7/2018 | |
| CN | 108520088 A | | 9/2018 | |
| CN | 110785682 A | | 2/2020 | |
| CN | 110916663 A | | 3/2020 | |
| CN | 111351813 A | * | 6/2020 | ............ G01N 13/00 |
| CN | 111721795 A | | 9/2020 | |
| CN | 112462311 A | * | 3/2021 | |

OTHER PUBLICATIONS

English translation of CN112462311A provided by Espacenet. (Year: 2023).*

Hongzhi Wang et al., "Design and Construction of a Fully-Opened Unilateral Nuclear Magnetic Resonance System", Chinese Journal of Magnetic Resonance, vol. 31, No. 4, Dec. 2014, pp. 488-501.

* cited by examiner

FIG. 1

```
┌─────────────────────────────────────────────┐
│  Acquiring a plurality of echo signals of an NMR pulse  │
│   sequence varying in echo spacing from a substance     │
│   to be measured, and processing the plurality of echo  │
│     signals to obtain a plurality of signals varying in │
│       transverse relaxation and diffusion attenuation   │
└─────────────────────────────────────────────┘
                        │
                        │
┌─────────────────────────────────────────────┐
│     In combination with prior knowledge, fitting the    │
│    plurality of signals varying in transverse relaxation│
│ and diffusion attenuation to obtain diffusion coefficient,│
│    transverse relaxation time or/and content weight of  │
│        components in the substance to be measured       │
└─────────────────────────────────────────────┘
```

NUCLEAR MAGNETIC RESONANCE SYSTEM-BASED SUBSTANCE MEASUREMENT METHOD AND SYSTEM

CROSS-REFERENCE TO RELATED APPLICATIONS

This application is a continuation of International Patent Application No. PCT/CN2020/130163, filed on Nov. 19, 2020, which claims the benefit of priority from Chinese Patent Application No. 202010611176.6, filed on Jun. 29, 2020. The content of the aforementioned application, including any intervening amendments thereto, is incorporated herein by reference in its entirety.

TECHNICAL FIELD

This application relates to substance measurement, and more particularly to a nuclear magnetic resonance system-based substance measurement method and system.

BACKGROUND

In the nuclear magnetic resonance (NMR), relaxation refers to the phenomenon that the nucleus that resonates and is in a high-energy state will quickly return to the original low-energy state when the radio frequency (RF) pulse stops. The recovery process is a relaxation process, which is an energy conversion process that takes time to reflect the interaction between protons in the proton system and between the proton and the environment. Under the action of RF pulses, all protons have the same phase, are all arranged in the same direction, and perform precession around the outer magnetic field with the same angular velocity (or angular frequency). When the RF pulse stops, the protons in the same phase will gradually appear phase difference between each other, that is, out of phase.

Protons are gradually dispersed from the same phase to reach uniform distribution, whose macroscopic manifestation is the changes of the transverse magnetization intensity vector $M_{xy}$. From a physical standpoint, the transverse relaxation process is a process of exchanging energy between homogeneous nuclei, also called the spin-spin relaxation process. Due to the interaction between proton spins, the transverse magnetization intensity $M_{xy}$ decays over time. After the action of 90° pulse, $M_{xy}$ satisfies formula (1):

$$M_{xy}(t)=M_{xymax}e^{-t/T_2} \quad (1)$$

In formula (1), $M_{xy}(t)$ is the transverse magnetization intensity at time t, $M_{xymax}$ is the transverse magnetization intensity at time 0, and t is the time calculated from the transverse magnetization intensity of $M_{xymax}$.

$T_2$ in the formula (1) is transverse relaxation time, also called spin-spin relaxation time.

Water molecules in biological tissues are constrained by the surrounding medium. After the NMR signal is excited, the diffusion movement of water molecules in the direction of the gradient magnetic field will attenuate the NMR signal. If the water molecules diffuse more freely along the direction of the gradient magnetic field, the diffusion distance will be larger during the application of the gradient magnetic field, the change in the magnetic field will be greater, and the attenuation of the tissue signal will be more obvious. Similar to $T_2$ attenuation, the attenuation caused by diffusion can be expressed as:

$$S(t)=S_{max}e^{-Dbt} \quad (2).$$

Since in NMR, the acquired signal intensity is proportional to the transverse magnetization vector, and $T_2$ and diffusion attenuation are comprehensively considered, the signal intensity and time satisfy:

$$S(t)=S_{max}e^{-Dbt} \cdot e^{-t/T_2} \quad (3)$$

In formulas (2) and (3), S(t) is the signal intensity acquired at time t, $S_{max}$ is the signal intensity at t=0, D is the diffusion coefficient of the substance, b is referred to b value which is a coefficient determined by the combination of diffusion weighted imaging and diffusion tensor imaging to describe the intensity of the diffusion gradient, duration time and application interval. The b value is larger indicating the more sensitive to diffusion.

Therefore, by measuring the $T_2$ time constant and diffusion coefficient corresponding to each component in substance, the NMR system can measure the content of various components in the substance, which can be used to analyze the special properties of the substance or be applied to clinical diagnosis.

D-T2 two-dimensional spectral analysis method is an NMR technology widely used in substance analysis. D-T2 two-dimensional spectral analysis method generally uses diffusion weighted module combined with Carr-Purcell-Meiboom-Gill (CPMG) to fast readout NMR sequence acquisition data of module. The common sequences are as follows: (a) Spin-Echo Carr-Purcell-Meiboom-Gill (SE-CPMG) sequence that is based on spin echo for diffusion gradient coding and reads out signal by ultra-fast CPMG sequence; (b) DSE-CPMG sequence that is based on the two-echo sequence for diffusion gradient coding and also reads out signal by ultra-fast CPMG sequence, which can reduce the impact of low-speed liquid flow; (c) STE-CPMG sequence that is based on the stimulated echo sequence for diffusion gradient coding, which can reduce the effect of $T_1$ recovery, when the $T_1/T_2$ of the detected object is small, the diffusion coefficient is measured by this sequence to improve the measurement accuracy.

Figure 1:
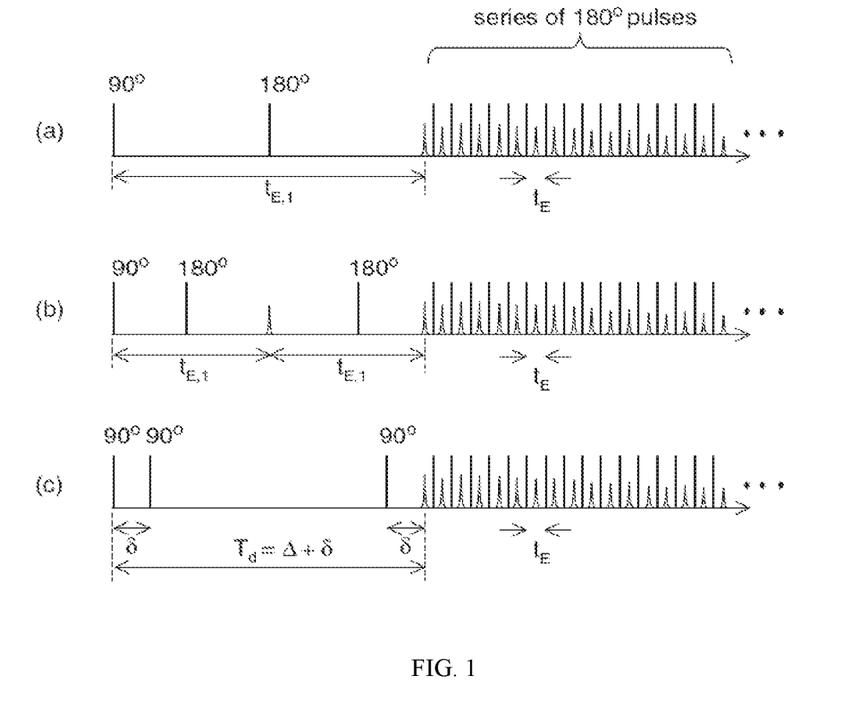
FIG. 1 schematically shows D-$T_2$ 2D NMR pulse sequence.

The D-T2 two-dimensional spectral analysis method needs to adjust the b value of the diffusion weighted module, collect tens to hundreds of sets of data, and then find D-T2 of the substance through the two-dimensional Inverse Laplace transform (ILT), that is, the diffusion coefficient-$T_2$ relaxation time distribution diagram, so as to obtain the composition information of the substance. The sequence of D-T2 spectroscopy measurements is shown in FIG. 1.

D-T2 two-dimensional spectral analysis method has the following disadvantages. (1) This method needs to collect a large amount of data, has the long collection time, and large data storage resource consumption. Due to the large amount of data, data processing has high hardware requirements, and often requires preprocessing of data and long operation time. (2) The inverse Laplace transform is sensitive to noise, the has unstable fitting results, and poor robustness of the algorithm.

SUMMARY

In view of the deficiencies in the prior art, this application provides a substance measurement method based on a nuclear magnetic resonance (NMR) system and system to solve or improve the problem of large amount of data processing.

In a first aspect, this application provides a substance measurement method based on an NMR system, including:

(a) acquiring a plurality of echo signals of an NMR pulse sequence varying in echo spacing from a substance to be measured, and processing the plurality of echo signals to obtain a plurality of signals varying in transverse relaxation and diffusion attenuation; and (b) in combination with prior knowledge, fitting the plurality of signals with transverse relaxation and diffusion attenuation to obtain diffusion coefficient, transverse relaxation time or/and content weight of components in the substance to be measured;

wherein the NMR pulse sequence is a Carr-Purcell-Meiboom-Gill (CPMG) sequence;

a gradient system of the NMR system includes a unilateral magnet, and a natural gradient magnetic field formed by the unilateral magnet is configured to perform diffusion encoding on the plurality of signals varying in transverse relaxation and diffusion attenuation; and the echo spacing and b satisfy:

$$b = -\frac{1}{12}\gamma^2 G_0^2 t_E^2; \quad (4)$$

wherein $G_0$ is a magnetic field gradient; $\gamma$ is a spin-magnetic ratio; $t_E$ is the echo spacing; and b is defined as b-value in NMR;

step (a) includes:

defining each of the plurality of echo signals as a four-dimensional array s (b', m, x, p), wherein the first dimension b' indexes an echo signal corresponding to the b-value in formula (4); the second dimension m indexes echo train length (ETL); the third dimension x indexes signal average; the fourth dimension p indexes sampling points of data in a single readout; and b', m, x and p are positive integers; and performing Fourier transform on fourth dimensions p in all four-dimensional arrays s (b', m, x, p); taking a low-frequency part as an average value; and averaging third dimensions x of the four-dimensional arrays s (b', m, x, p) to obtain the plurality of signals varying in transverse relaxation and diffusion attenuation.

In an embodiment, the step (b) is performed through steps of:

fitting the plurality of signals varying in transverse relaxation and diffusion attenuation to obtain the diffusion coefficient, transverse relaxation time or/and content weight of components in the substance to be measured through the following formula:

$$\operatorname{argmin}\left\|\sum_{n=0,1,2,3...} a_{3n+1} e^{(-a_{3n+2}t - a_{3n+3}bt)} + k - s\right\|; \quad (5)$$

wherein a constraint of formula (5) is expressed as:

$$\begin{cases} a_{3n+1LB} < a_{3n+1} < a_{3n+1UB} \\ a_{3n+2LB} < a_{3n+2} < a_{3n+2UB} \\ a_{3n+3LB} < a_{3n+3} < a_{3n+3UB} \\ k_{LB} < k < k_{UB} \end{cases};$$

wherein n is an integer greater than or equal to zero; $a_{3n+1}$ is the content weight of individual components in the substance to be measured; $a_{3n+2}$ is a reciprocal of a transverse relaxation time constant $T_2$ of individual components in the substance to be measured; $a_{3n+3}$ is the diffusion coefficient of individual components in the substance to be measured; k represents noise; s represents an echo signal of the NMR pulse sequence; represents $\|\ \|$ 2-norm; and in the constraint, LB and UB are lower bound and upper bound obtained by the prior knowledge, respectively.

This application further provides a system for implementing the substance measurement method above, including:

a console;

a magnet module; and an NMR system;

wherein the console is configured to send a command for transmitting an NMR pulse sequence, receive an echo signal of the NMR pulse sequence, analyze and process the echo signal of the NMR pulse sequence to obtain a signal with transverse relaxation and diffusion attenuation, and fit the signal with transverse relaxation and diffusion attenuation to obtain a diffusion coefficient, transverse relaxation time or/and content weight of individual components in a substance to be measured;

the magnet module is configured to apply a natural gradient magnetic field to the substance to be measured; and the NMR system is configured to receive the command for transmitting the NMR pulse sequence, transmit the NMR pulse sequence to the substance to be measured according to the command, and receive and feed back the echo signal of the NMR pulse sequence to the console.

In an embodiment, the NMR system includes an NMR spectrometer and a radio frequency system;

the NMR spectrometer is configured to receive the command for transmitting the NMR pulse sequence, transmit the NMR pulse sequence according to the command, receive the echo signal of the NMR pulse sequence fed back by the radio frequency system, and feed back the echo signal of the NMR pulse sequence to the console; and the radio frequency system is configured to process the NMR pulse sequence for application to the substance to be measured, process the echo signal of the NMR pulse sequence for feedback to the console, perform switching between a mode for transmitting the NMR pulse sequence and a mode for receiving the echo signal of the NMR pulse sequence, and transmit the NMR pulse sequence or receive the echo signal of the NMR pulse sequence.

In an embodiment, the radio frequency system includes a transmit-receive switch module and a radio-frequency coil;

wherein the transmit-receive switch module is in communication with the NMR spectrometer, and is configured to perform switching between the mode for transmitting the NMR pulse sequence and the mode for receiving the echo signal of the NMR pulse sequence; and the radio-frequency coil is in communication with the transmit-receive switch module; and the radio-frequency coil is configured to generate an excitation center frequency for the substance to be measured when the transmit-receive switch module is switched to the mode for transmitting the NMR pulse sequence, and to receive the echo signal of the NMR pulse sequence when the transmit-receive switch module is switched to the mode for receiving the echo signal of the NMR pulse sequence.

In an embodiment, the transmit-receive switch module is a transmit-receive switch.

In an embodiment, the magnet module includes a unilateral magnet.

A substance measurement method and system in this application acquire a plurality of echo signals of an NMR pulse sequence varying in echo spacing from a substance to be measured, and process the plurality of echo signals to obtain a plurality of signals with transverse relaxation and diffusion attenuation. In combination with prior knowledge, the plurality of signals with transverse relaxation and diffusion attenuation are fit to obtain diffusion coefficient, transverse relaxation time or/and content weight of components in the substance to be measured. Obviously, it is not necessary to collect a large amount of data to measure the diffusion coefficient, transverse relaxation time or/and content weight of the components in the substance to be measured, so that the substance measurement method and system can be applied to property analysis of the substance or clinical diagnosis.

BRIEF DESCRIPTION OF THE DRAWINGS

In order to explain the technical solutions of the disclosure more clearly, the drawings needed in the description of the embodiments of the disclosure will be briefly introduced below.

DETAILED DESCRIPTION OF EMBODIMENTS

The disclosure will be described in detail below with reference to the embodiments and accompanying drawings to make objects, technical solutions and advantages of the disclosure clearer. It should be understood that these embodiments are merely illustrative, and are not intended to limit the disclosure.

A substance measurement method based on a nuclear magnetic resonance (NMR) system and system provided herein solve or improve the problem of large amount of data processing in prior art. The substance measurement method and system are conceived based on the same invention. Since the principles of the method and the system to solve the problem are similar, the implementation of the system and the method can be referred to each other, and the same description will not be repeated.

The term "plurality" in this disclosure refers to two or more. In addition, the terms "first" and "second" are merely for distinguishment, and cannot be understood as indicating or implying relative importance, or implying an order of the elements referred to.

Figure 2:
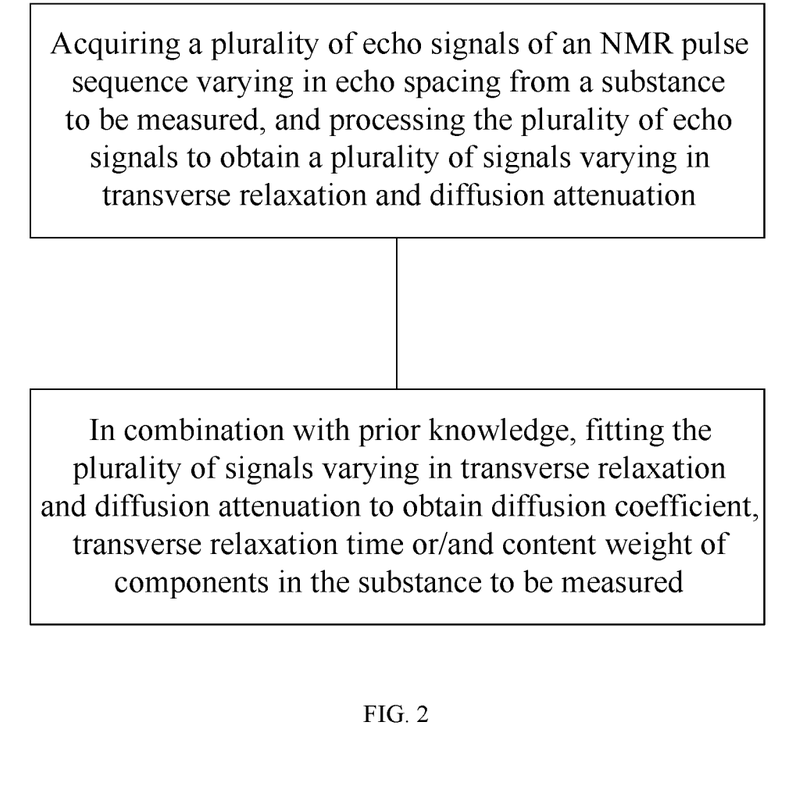
FIG. 2 is a flow chart of a substance measurement method according to an embodiment of the present disclosure.

Referring to FIG. 2, this application provides a substance measurement method based on an NMR system, which is performed as follows.

(a) A plurality of echo signals of an NMR pulse sequence varying in echo spacing are acquired from a substance to be measured, and the plurality of echo signals are processed to obtain a plurality of signals varying in transverse relaxation and diffusion attenuation.

(b) In combination with prior knowledge, the plurality of signals with transverse relaxation and diffusion attenuation is fit to obtain diffusion coefficient, transverse relaxation time or/and content weight of components in the substance to be measured.

The substance measurement method and system solve or improve the problem of large amount of data processing in the prior art and can be applied to the property analysis of the substance or clinical diagnosis.

The method in the disclosure obtains several groups of the signals with transverse relaxation and diffusion attenuation by acquiring several groups (such as less than ten groups) of echo signals of an NMR pulse sequence varying in echo spacing. In combination with prior knowledge of the components in the substance to be measured, the signals with transverse relaxation and diffusion attenuation are fitted to obtain the diffusion coefficient, transverse relaxation time constant or/and content weight of components in the substance to be measured. A signal processing model is established to fit the signals.

In order to make the method in this embodiment simultaneously fit the diffusion coefficient, the transverse relaxation time constant, and the content weight of components in the two substances, the following optional embodiments are provided.

Figure 4:
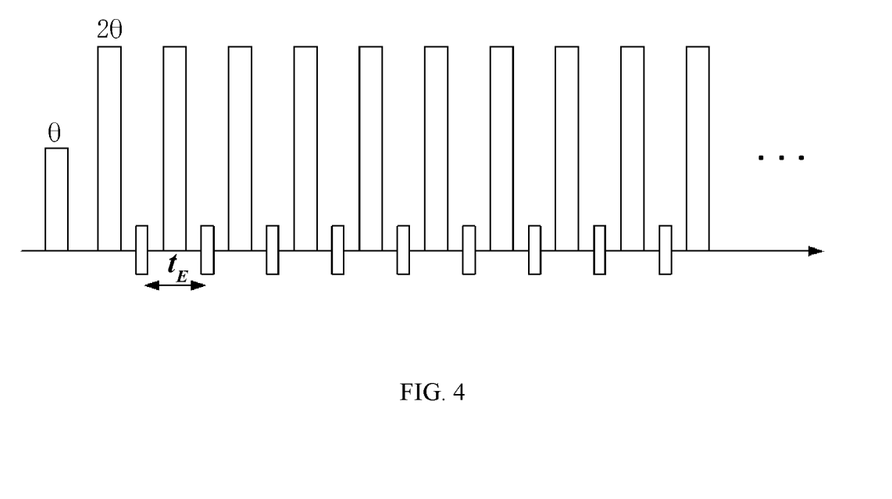
FIG. 4 illustrates an NMR pulse sequence according to an embodiment of the present disclosure.

In this embodiment, the NMR pulse sequence is a Carr-Purcell-Meiboom-Gill (CPMG) sequence, as shown in FIG. 4.

A gradient system of the NMR system includes a unilateral magnet, and a natural gradient magnetic field formed by the unilateral magnet is configured to perform diffusion encoding on the signals varying in transverse relaxation and diffusion attenuation. The echo spacing and b satisfy:

$$b = -\frac{1}{12}\gamma^2 G_0^2 t_E^2, \tag{4}$$

where $G_0$ is a magnetic field gradient; $\gamma$ is a spin-magnetic ratio; $t_E$ is the echo spacing; and b is commonly defined as b-value in NMR.

Optionally, the gradient system of the NMR system includes the unilateral magnet, and the unilateral magnet has a constant gradient field. Therefore, when the gradient system of the NMR system includes the unilateral magnet, $G_0$, or $\gamma$ is a fixed value. At this point, b is only related to the echo spacing $t_E$, so that b can be adjusted by controlling the size of $t_E$.

In order to facilitate automatic processing by computer, the step (a) includes the following steps. Each of the plurality of echo signals are defined as a four-dimensional array s (b', m, x, p). The first dimension b' indexes an echo signal corresponding to the b-value in formula (4). A second dimension m indexes echo train length (ETL). The third dimension x indexes signal average. A fourth dimension p indexes sampling points of data in a single readout. b', m, x and p are positive integers.

Among them, the third dimension x indexes signal average. When in use, the signals need to be collected multiple times to average to improve the signal-to-noise ratio. The signal average x is the number of acquisitions required to improve the signal-to-noise ratio.

Fourier transform is performed on fourth dimensions p in all four-dimensional arrays s (b', m, x, p). A low-frequency part is taken as an average value. The third dimensions x of the four-dimensional arrays s (b', m, x, p) are averaged to obtain the plurality of signals with transverse relaxation and diffusion attenuation.

After Fourier transform and averaging, the four-dimensional array s (b', m, x, p) signal becomes a two-dimensional signal s (b', m). The two-dimensional signal s (b', m) is the signal attenuation curve of the intensity with time collected at different echo spacings. The signal with transverse relaxation and diffusion attenuation, such as s (1, :) is a curve of signal intensity attenuation with transverse relaxation time corresponding to the first echo spacing.

In this embodiment, the step (b) is performed through the following steps.

The plurality of signals varying in transverse relaxation and diffusion attenuation are fit to obtain the diffusion coefficient, transverse relaxation time or/and content weight of components in the substance to be measured through the following formula:

$$\operatorname{argmin} \left\| \sum_{n=0,1,2,3...} a_{3n+1} e^{(-a_{3n+2}t - a_{3n+3}bt)} + k - s \right\|. \quad (5)$$

A constraint of formula (5) is expressed as:

$$\begin{cases} a_{3n+1LB} < a_{3n+1} < a_{3n+1UB} \\ a_{3n+2LB} < a_{3n+2} < a_{3n+2UB} \\ a_{3n+3LB} < a_{3n+3} < a_{3n+3UB} \\ k_{LB} < k < k_{UB} \end{cases}.$$

In the formula (5), n is an integer greater than or equal to zero. $a_{3n+1}$ is the content weight of individual components in the substance to be measured. $a_{3n+2}$ is a reciprocal of a transverse relaxation time constant $T_2$ of individual components in the substance to be measured. $a_{3n+3}$ is the diffusion coefficient of individual components in the substance to be measured. k represents noise. s represents an echo signal of the NMR pulse sequence. $\| \ \|$ represents 2-norm. In the constraint. LB and UB are lower bound and upper bound obtained by the prior knowledge, respectively.

k is a noise-related parameter, but k can also be a noise-related expression or a noise-related probability model.

The specific embodiments will be further described as follow.

In this embodiment, components of two substances are determined, that is, n takes 0 and 1 respectively. The formula (5) can be simplified to the following formula (6).

$$\operatorname{argmin} \left\| \left( a_1 e^{(-a_2 t - a_3 bt)} + a_4 e^{(-a_5 t - a_6 bt)} + k \right) - s \right\|. \quad (6)$$

A constraint of the formula (6) is expressed as:

$$\begin{cases} a_{1LB} < a_1 < a_{1UB} \\ a_{2LB} < a_2 < a_{2UB} \\ a_{3LB} < a_3 < a_{3UB} \\ a_{4LB} < a_4 < a_{4UB} \\ a_{5LB} < a_5 < a_{5UB} \\ a_{6LB} < a_6 < a_{6UB} \\ k_{LB} < k < k_{UB} \end{cases}$$

LB and UB are lower bound and upper bound obtained by the prior knowledge, respectively.

Among them, $a_1$ and $a_4$ are the content weights of individual components in substances 1 and 2. $a_2$ and $a_5$ are the reciprocals of the transverse relaxation time constant $T_2$ of substances 1 and 2. $a_3$ and $a_6$ are the diffusion coefficients of individual components in substances 1 and 2. k is the mean noise. s is the echo signal of the NMR pulse sequence. $\| \ \|$ represents 2-norm That is, the content weight, the reciprocal of transverse relaxation time constant $T_2$ and the diffusion coefficient of the substance 1 are $a_1$, $a_2$ and $a_3$, respectively. The content weight, the reciprocal of transverse relaxation time constant $T_2$ and the diffusion coefficient of the substance 2 were $a_4$, $a_5$ and $a_6$, respectively. If there is a variety of substances, and so on.

By setting different $t_E$, the acquired signal s can be represented as a four-dimensional array, where the first dimension is acquisition of different b-values corresponding to different echo spacings. In this embodiment, the first dimension size is 2. The second dimension is the echo chain length. The third dimension indexes signal average. The fourth dimension indexes sampling points of data in a single readout.

After performing Fourier transform on the fourth dimension, the low-frequency part is taken as the average, and then the third dimension is averaged to obtain two attenuation curves with different b-values (echo spacing time). By bringing the signal s measured at two different echo spacings into the formula (6), according to the previous conditions such as the diffusion coefficient of the two substances to be sought and the upper and lower bounds of the approximate value of the transverse relaxation time constant $T_2$, the range of fitting results of $a_1$-$a_6$ and k can be determined, so as to accurately solve the unknown quantity in the formula.

Figure 5:
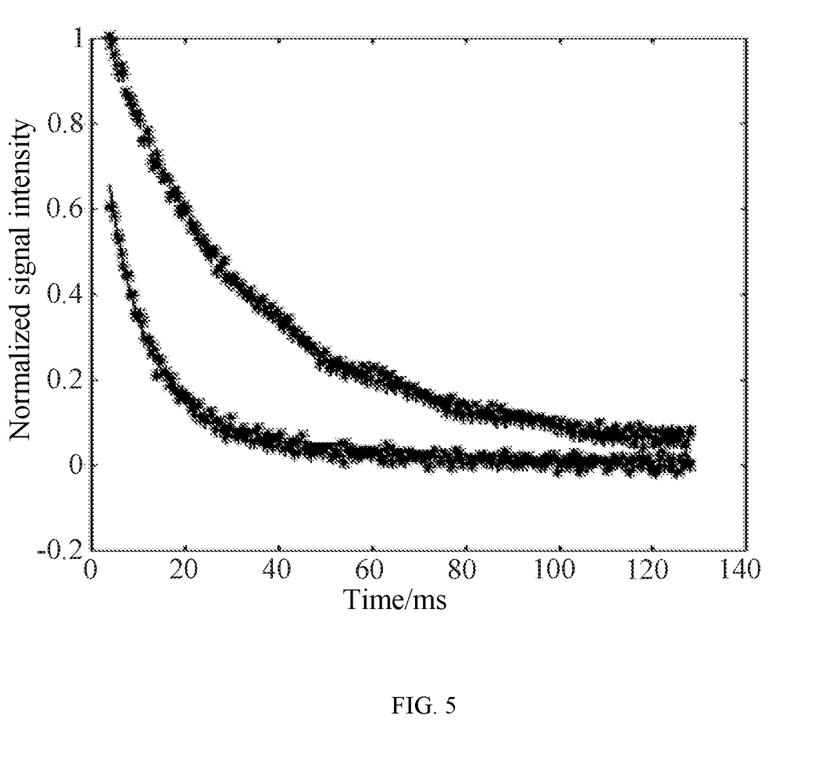
FIG. 5 shows fitted curves of two sets of signals varying in $t_E$ value collected in an embodiment of the present disclosure.

As shown in FIG. 5, in this typical setup, the diffusion coefficient, relaxation time constant $T_2$, and fat content of the human liver were measured. The magnetic field of the unilateral magnet of the NMR system was 0.08 T, and the constant gradient field was about 1.1 T/m. Two different sets of echo spacings (500 us and 1100 us) with the echo chain length of 256 times and an average of 64 times were measured, and 64 points were acquired per echo. The repeat time TR was 1000 ms, and the total acquisition time was about 2 min. Combined with the prior knowledge of liver tissue and fat, the upper and lower bounds of $a_1 \sim a_6$ and k were set to fit and obtain the fat ratio 13.5212%, fat $T_2$=115 ms, liver tissue $T_2$=39.9 ms, fat diffusion coefficient 2.0 $e^{-5}$ mm$^2$/s, and liver tissue diffusion coefficient 1.2109 $e^{-3}$ mm$^2$/s.

Thus, the method in the disclosure uses the traditional CPMG sequence to adjust the echo spacing alone, the signal processing after the measurement sequence is simple, and the substance content can be measured without collecting a large amount of data. Thus, the method has the advantages of short acquisition time, low storage requirements, low data processing time, stable fitting results, and high repeatability.

This application further provides a system for implementing the substance measurement method above, including a console, a magnet module, and an NMR system.

The console is configured to send a command for transmitting an NMR pulse sequence, receive an echo signal of the NMR pulse sequence, analyze and process the echo signal of the NMR pulse sequence to obtain a signal with transverse relaxation and diffusion attenuation, and fit the signal with transverse relaxation and diffusion attenuation to obtain a diffusion coefficient, transverse relaxation time or/and content weight of individual components in a substance to be measured.

The magnet module is configured to apply a natural gradient magnetic field to the substance to be measured.

The NMR system is configured to receive the command for transmitting the NMR pulse sequence, transmit the NMR pulse sequence to the substance to be measured according to the command, and receive and feed back the echo signal of the NMR pulse sequence to the console.

In this embodiment, the NMR system includes an NMR spectrometer and a radio frequency system.

The NMR spectrometer is configured to receive the command for transmitting the NMR pulse sequence, transmit the NMR pulse sequence according to the command, receive the echo signal of the NMR pulse sequence fed back by the radio frequency system, and feed back the echo signal of the NMR pulse sequence to the console.

The radio frequency system is configured to process the NMR pulse sequence for application to the substance to be measured, process the echo signal of the NMR pulse sequence for feedback to the console, perform switching between a mode for transmitting the NMR pulse sequence and a mode for receiving the echo signal of the NMR pulse sequence, and transmit the NMR pulse sequence or receive the echo signal of the NMR pulse sequence.

In an embodiment, the radio frequency system includes a transmit-receive switch module and a radio-frequency (RF) coil.

The transmit-receive switch module is in communication with the NMR spectrometer and configured to perform switching between the mode for transmitting the NMR pulse sequence and the mode for receiving the echo signal of the NMR pulse sequence.

The radio-frequency coil is in communication with the transmit-receive switch module. The radio-frequency coil is configured to generate an excitation center frequency for the substance to be measured when the transmit-receive switch module is switched to the mode for transmitting the NMR pulse sequence, and to receive the echo signal of the NMR pulse sequence when the transmit-receive switch module is switched to the mode for receiving the echo signal of the NMR pulse sequence.

Figure 3:
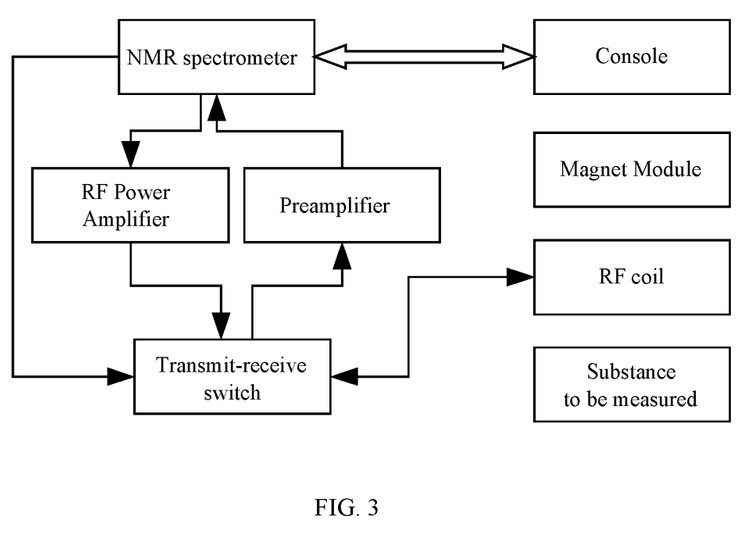
FIG. 3 structurally illustrates a substance measurement system according to an embodiment of the present disclosure.

As shown in FIG. 3, a working process of system is as follows.

The console sends the command for transmitting an NMR pulse sequence to the nuclear magnetic resonance spectrometer. According to the command for transmitting the NMR pulse sequence, the nuclear magnetic resonance spectrometer transmits the NMR pulse sequence, such as Carr-Purcell-Meiboom-Gill (CPMG) sequence. After the NMR pulse sequence is processed by the RF power amplifier, the transmit-receive switch module (such as the transmit-receive switch) is switched to the mode for transmitting the NMR pulse sequence and sends the processed NMR pulse sequence to the RF coil. The RF coil acts on the substance to be measured under the gradient magnetic field of the magnet module (such as a unilateral permanent magnet). Then, the transmit-receive switch module is switched to the mode for receiving the echo signal of the NMR pulse sequence, and the transmit-receive switch module receives the echo signal of the NMR pulse sequence of the substance to be measured through the RF coil and feeds back to the NMR spectrometer after processed by a preamplifier. The NMR spectrometer transmits the echo signal of the NMR pulse sequence to the console. The echo signals of the NMR pulse sequence of two or more substances to be measured with different echo spacings are acquired in the above way, and so on until all acquisitions are complete. After the acquisitions are completed, the console analyzes and processes the echo signal to obtain the signal with transverse relaxation and diffusion attenuation, and fits the signal with transverse relaxation and diffusion attenuation to obtain the diffusion coefficient, transverse relaxation time or/and content weight of the components in the substance to be measured.

In this embodiment, the transmit-receive switch module is a transmit-receive switch. Optionally, the magnet module includes a unilateral magnet. The magnet module uses a unilateral magnet without the need for an additional gradient system, thereby reducing the complexity and hardware cost of the system.

Thus, the system of the disclosure acquires echo signals of the NMR pulse sequence varying in echo spacing from two or more substances to be measured. After the acquisition is completed, the signal with transverse relaxation and diffusion attenuation is obtained by analyzing and processing the echo signals through the console. The signals with transverse relaxation and diffusion attenuation are fitted to obtain the diffusion coefficient, transverse relaxation time or/and content weight of the components in the substance to be measured. The content of substance can be measured, which has a simple signal processing without acquiring a large amount of data. Thus, the system has the advantages of short acquisition time, low storage requirements, low data processing time, and stable fitting results and high repeatability.

It should be understood by those skilled in the art that all or part of the steps to implement the above method may be completed by the hardware associated with the program command. The aforementioned program may be stored in a computer-readable storage medium. When executed, the program performs steps of the above method. The aforementioned storage medium includes ROM, RAM, disk or optical disk and other media that can store program code.

It should be understood by those skilled in the art that embodiments in the disclosure may be set as methods, systems, or computer program products. Accordingly, the disclosure may take the form of a complete hardware embodiment, a complete software embodiment, or a combination of software and hardware embodiments. Further, the disclosure may take the form of a computer program product implemented on one or more computer-usable storage media (including but not limited to disk memory, CD-ROM, and optical memory) including computer-usable program code.

The disclosure is described with reference to a flowchart and/or block diagram of a method, apparatus (system), and computer program product according to embodiments of the disclosure. It should be understood that each process or/and the combination of processes in the flowchart can be implemented by computer program instructions. Or, each process or/and the combination of processes in the block diagram can be implemented by computer program instructions. These computer program instructions may be provided to a processor of a general-purpose computer, a special purpose computer, an embedded processor, or other programmable data processing device to generate a machine, such that the instructions executed by the processor of a computer or other programmable data processing device produce a device for implementing the functions specified in the flowchart, or one or more processes in one box or more boxes of the block diagram.

These computer program instructions may also be stored in computer-readable memory capable of booting a computer or other programmable data processing device to work in a particular manner, such that the instructions stored in the computer-readable memory produce manufactured products including an instruction device. The instruction device implements the function specified in one or more processes in the flow chart and/or one box or more boxes of the block diagram.

These computer program instructions may also be loaded into a computer or other programmable data processing device, such that a series of operational steps are performed on a computer or other programmable device to produce computer-implemented processing, so that the instructions executed on a computer or other programmable device provide steps for achieving the functions specified in one or more processes in the flow chart and/or one box or more boxes of the block diagram.

Described above are merely preferred embodiments of the disclosure, and are not intended to limit the disclosure. Though the disclosure has been described in detail above, those skilled in the art can still make various replacements and modifications to the embodiments provided herein. It should be understood that those modifications and replacements made by those skilled in the art without departing from the spirit of the disclosure should fall within the scope of the disclosure defined by the appended claims.

What is claimed is:

1. A substance measurement method based on a nuclear magnetic resonance (NMR) system, comprising:
   (a) acquiring a plurality of echo signals of an NMR pulse sequence varying in echo spacing from a substance to be measured, and processing the plurality of echo signals to obtain a plurality of signals varying in transverse relaxation and diffusion attenuation; and
   (b) in combination with prior knowledge, fitting the plurality of signals with transverse relaxation and diffusion attenuation to obtain diffusion coefficient, transverse relaxation time or/and content weight of components in the substance to be measured;
   wherein the NMR pulse sequence is a Carr-Purcell-Meiboom-Gill (CPMG) sequence;
   a gradient system of the NMR system comprises a unilateral magnet, and a gradient magnetic field formed by the unilateral magnet is configured to perform diffusion encoding on the plurality of signals varying in transverse relaxation and diffusion attenuation; and the echo spacing and b satisfy:

$$b = -\frac{1}{12}\gamma^2 G_0^2 t_E^2; \quad (4)$$

wherein $G_0$ is a magnetic field intensity of the gradient magnetic field; $\gamma$ is a spin-magnetic ratio; $t_E$ is the echo spacing; and b is defined as b-value in NMR;
   step (a) comprises:
   defining each of the plurality of echo signals as a four-dimensional array s (b', m, x, p), wherein a first dimension b' indexes an echo signal corresponding to the b-value in formula (4); a second dimension m indexes echo train length (ETL); a third dimension x indexes signal average of the plurality of echo signals; a fourth dimension p indexes sampling points of data in a single readout; and b', m, x and p are positive integers; and
   performing Fourier transform on fourth dimensions p in all four-dimensional arrays s (b', m, x, p); taking a low-frequency part as an average value; and averaging third dimensions x of the four-dimensional arrays s (b', m, x, p) to obtain the plurality of signals varying in transverse relaxation and diffusion attenuation.

2. The substance measurement method of claim 1, wherein the step (b) is performed through steps of:
   fitting the plurality of signals varying in transverse relaxation and diffusion attenuation to obtain the diffusion coefficient, transverse relaxation time or/and content weight of components in the substance to be measured through the following formula:

$$\mathrm{argmin}\left\|\sum_{n=0,1,2,3...} a_{3n+1} e^{(-a_{3n+2}t - a_{3n+3}bt)} + k - s\right\|; \quad (5)$$

wherein a constraint of formula (5) is expressed as:

$$\begin{cases} a_{3n+1LB} < a_{3n+1} < a_{3n+1UB} \\ a_{3n+2LB} < a_{3n+2} < a_{3n+2UB} \\ a_{3n+3LB} < a_{3n+3} < a_{3n+3UB} \\ k_{LB} < k < k_{UB} \end{cases};$$

wherein n is an integer greater than or equal to zero; $a_{3n+1}$ is the content weight of individual components in the substance to be measured; $a_{3n+2}$ is a reciprocal of a transverse relaxation time constant $T_2$ of individual components in the substance to be measured; $a_{3n+3}$ is the diffusion coefficient of individual components in the substance to be measured; k represents noise; s represents an echo signal of the NMR pulse sequence; $\|\ \|$ represents 2-norm; in the constraint, LB and UB are lower bound and upper bound obtained by the prior knowledge, respectively; t is a time point at which the echo signal of the NMR pulse sequence is acquired; and b is defined as the b-value in NMR.

3. An NMR-based system for performing the substance measurement method of claim 1, comprising:
   a console;
   a magnet module; and
   the NMR system;
   wherein the console is configured to send a command for transmitting the NMR pulse sequence, receive the echo signal of the NMR pulse sequence, analyze and process the echo signal of the NMR pulse sequence to obtain the signal with transverse relaxation and diffusion attenuation, and fit the signal with transverse relaxation and diffusion attenuation to obtain the diffusion coefficient, transverse relaxation time or/and content weight of individual components in the substance to be measured;
   the magnet module is configured to apply the gradient magnetic field to the substance to be measured; and the gradient magnetic field is configured to perform diffusion encoding on the plurality of signals varying in the transverse relaxation and diffusion attenuation; and the echo spacing and b satisfy the formula (4); and
   the NMR system is configured to receive the command for transmitting the NMR pulse sequence, transmit the NMR pulse sequence to the substance to be measured according to the command, and receive and feed back the echo signal of the NMR pulse sequence to the console.

4. The NMR-based system of claim 3, wherein the NMR system comprises an NMR spectrometer and a radio frequency system;
   the NMR spectrometer is configured to receive the command for transmitting the NMR pulse sequence, transmit the NMR pulse sequence according to the command, receive the echo signal of the NMR pulse sequence fed back by the radio frequency system, and feed back the echo signal of the NMR pulse sequence to the console; and the radio frequency system is configured to process the NMR pulse sequence for application to the substance to be measured, process the echo signal of the NMR pulse sequence for feedback to the console, perform switching between a mode for transmitting the NMR pulse sequence and a mode for receiving the echo signal of the NMR pulse sequence, and transmit the NMR pulse sequence or receive the echo signal of the NMR pulse sequence.

5. The NMR-based system of claim 4, wherein the radio frequency system comprises a transmit-receive switch module and a radio-frequency coil;

wherein the transmit-receive switch module is in communication with the NMR spectrometer, and is configured to perform switching between the mode for transmitting the NMR pulse sequence and the mode for receiving the echo signal of the NMR pulse sequence; and the radio-frequency coil is in communication with the transmit-receive switch module; and the radio-frequency coil is configured to generate an excitation center frequency for the substance to be measured when the transmit-receive switch module is switched to the mode for transmitting the NMR pulse sequence, and to receive the echo signal of the NMR pulse sequence when the transmit-receive switch module is switched to the mode for receiving the echo signal of the NMR pulse sequence.

6. The NMR-based system of claim 5, wherein the transmit-receive switch module is a transmit-receive switch.

7. The NMR-based system of claim 6, wherein the magnet module comprises the unilateral magnet.

\* \* \* \* \*